United States Patent
Balugani et al.

(10) Patent No.: US 6,478,774 B1
(45) Date of Patent: Nov. 12, 2002

(54) DEVICE FOR POSTOPERATIVE AUTOTRANSFUSION, PARTICULARLY IN HEART SURGERY

(75) Inventors: Fabio Balugani, Cavezzo (IT); Paolo Fontanili, Correggio (IT)

(73) Assignee: Eurosets S.r.l., Medolla (IT)

( * ) Notice: Subject to any disclaimer, the term of this patent is extended or adjusted under 35 U.S.C. 154(b) by 174 days.

(21) Appl. No.: 09/711,963

(22) Filed: Nov. 15, 2000

(30) Foreign Application Priority Data

Nov. 18, 1999 (IT) ........................................ MN99A0050

(51) Int. Cl.⁷ ................................................ A61M 1/00
(52) U.S. Cl. ........................... 604/151; 604/319; 422/44
(58) Field of Search ................................ 604/151, 5.01, 604/321, 319, 317, 6.15, 7; 422/44

(56) References Cited

U.S. PATENT DOCUMENTS

| | | | | |
|---|---|---|---|---|
| 4,838,872 A | * | 6/1989 | Sherlock | 604/319 |
| 4,929,244 A | * | 5/1990 | Swisher | 604/319 |
| 4,994,022 A | * | 2/1991 | Steffler et al. | 604/7 |
| 5,024,613 A | * | 6/1991 | Vasconcellos et al. | 604/6.15 |
| 5,374,257 A | * | 12/1994 | Drainville et al. | 604/319 |
| 5,588,958 A | * | 12/1996 | Cunningham et al. | 604/6.15 |
| 5,722,964 A | * | 3/1998 | Herweck et al. | 604/317 |
| 5,885,261 A | * | 3/1999 | Longo et al. | 604/319 |
| 5,989,234 A | * | 11/1999 | Valerio et al. | 604/321 |
| 6,017,493 A | * | 1/2000 | Cambron et al. | 422/44 |
| 6,113,554 A | * | 9/2000 | Glicher et al. | 600/573 |
| 6,315,751 B1 | * | 11/2001 | Cosgrove et al. | 604/5.01 |

\* cited by examiner

Primary Examiner—Teresa Walberg
Assistant Examiner—Leonid M Fastovsky
(74) Attorney, Agent, or Firm—Guido Modiano; Albert Josif; Daniel O'Byrne

(57) ABSTRACT

A device for postoperative autotransfusion particularly in heart surgery, comprising elements adapted to act simultaneously at least on tubes that are connected to the atmosphere and to a drainage system of a patient, so as to selectively provide a condition in which the tube connected to the atmosphere is closed and the tube connected to the patient drainage system is open, and a condition in which the tube connected to the atmosphere is open and the tube connected to the patient drainage system is closed.

8 Claims, 4 Drawing Sheets

DEVICE FOR POSTOPERATIVE AUTOTRANSFUSION, PARTICULARLY IN HEART SURGERY

BACKGROUND OF THE INVENTION

The present invention relates to a device for postoperative autotransfusion, particularly in heart surgery.

It is known that the technique of postoperative autotransfusion is used particularly in heart surgery and consists in collecting the blood spilled by the drainages of the surgical wound, evacuating it together with air from the pleural-mediastinal cavity of a patient in order to reinfuse it into the patient after filtration.

The classical method, which can be performed without problems in the first hours after the operation, when the patient is under assisted ventilation, requires the adoption of a system which comprises a chamber which is connected to a vacuum generator, typically provided as a water seal valve which ensures downstream, in a known manner, the constancy of the degree of vacuum, and the direct connection thereof to a blood collection chamber which is connected to the drainages of the patient and thus receives the blood by way of the suction determined by the vacuum that is present therein.

In an evolution of the system, a water seal has been introduced in an intermediate position with respect to the above-described suction control and blood collection chambers; such seal ensures the monitoring of the air arriving from the patient and acts as a reflux-preventing valve which prevents the entry of air at atmospheric pressure into the pleural cavity, so as to avoid collapse of the lungs.

In this configuration, the system is used without problems both when the patient is under assisted ventilation and when the ventilation ceases and the patient breathes autonomously, and is further such as to allow a variation in the operating protocol which is sometimes adopted for clinical reasons and consists in so-called gravity drainage, in which the system is disconnected from the vacuum generator and the blood mixed with air is made to reach the collection chamber by gravity.

In order to provide this variation, it is important to provide, within the water seal, a maximum negative pressure valve, adapted to prevent external events, such as coughing of the patient or squeezing of the tubes on the part of the operators, from bringing the blood collection chamber to excessive negative pressure values.

The system provided with the above-described three chambers, respectively for suction control, water sealing and blood collection, has considerable positive features, but in the currently known embodiment it has some drawbacks which consist of the presence of pumping means for transferring the blood from the collection chamber to a bag which is meant to be connected to the patient for reinfusion, or directly to the patient, and further has a certain operating complexity which the operator encounters in various steps of operation.

SUMMARY OF THE INVENTION

The aim of the present invention is therefore to provide a device for postoperative autotransfusion particularly in closed-circuit heart surgery which provides maximum simplicity of operation, with assurance of absolute safety against the possibility of errors, in any functional condition, and further allows to transfer the blood from the collection chamber to a normal bag to be connected to the patient without requiring the adoption of any pumping means.

Within this aim, an object of the invention is to provide a device in which the bidirectional passage of liquids between the water seal and the blood collection chamber is prevented and in which sterilization of the air that passes from one chamber to the other is ensured.

This aim and this and other objects which will become better apparent hereinafter are achieved by a device for postoperative autotransfusion particularly in heart surgery, according to the invention, which comprises, functionally connected in a monolithic unit: a suction control chamber, which is adapted to be connected to a vacuum generator by means of a tube; a blood collection chamber, which is provided at the bottom with a cock adapted to be connected to a bag and is adapted to be connected by means of at least one tube to the drainage system of a patient; and a water seal, which is interposed between said chambers and comprises two ducts which are interconnected at the lower end and are connected, at the upper end, respectively to the suction control chamber and to the blood collection chamber, a union being provided proximate to the end that is connected to said blood collection chamber, said union being connected to the atmosphere by means of a tube, characterized in that it comprises means which are adapted to act simultaneously on said tubes connected to the atmosphere and to the drainage system of a patient, so as to selectively provide a condition in which the tube connected to the atmosphere is closed and the tube connected to the patient drainage system is open, and a condition in which said tube connected to the atmosphere is open and said tube connected to the patient drainage system is closed.

In a device comprising the three chambers described above, respectively the suction control chamber, the water seal chamber and the blood collection chamber, advantageously there is, between the water seal and the blood collection chamber, a membrane which is hydrophobic and as such prevents the bidirectional flow of liquids and sterilizes the air that passes through it.

BRIEF DESCRIPTION OF THE DRAWINGS

Further characteristics and advantages of the present invention will become better apparent from the following detailed description of a preferred but not exclusive embodiment thereof, illustrated only by way of non-limitative example in the accompanying drawings, wherein.

DESCRIPTION OF THE PREFERRED EMBODIMENTS

Figure 1:
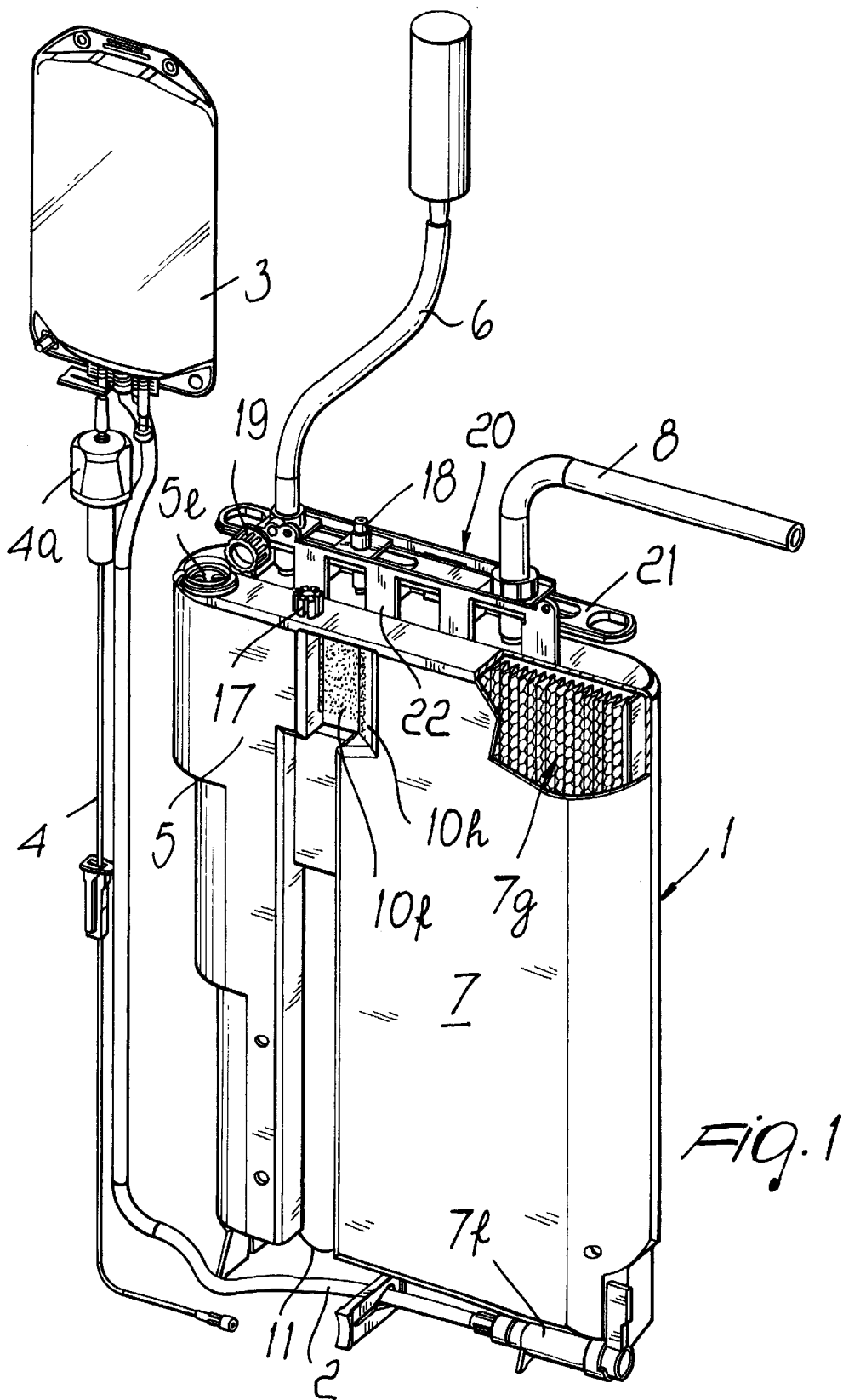
FIG. 1 is a perspective view of the device according to the invention.

With reference to the figures, the reference numeral 1 generally designates the device, which is connected, by means of a tube 2, to a bag 3, which is designed to receive blood to be reinfused to the patient by means of a line 4, which is provided with a filter 4a.

The device 1, made of blood-compatible and transparent material, comprises first of all a suction control chamber 5, which is delimited by side walls 5a and 5b, by a front wall, which is omitted in the drawing, by a rear wall, and finally by an inclined bottom 5c.

The chamber, which is provided in an upward region with a labyrinth 5d described hereinafter, is designed to be filled in a known manner with water up to a certain level by means of a plug 5e, which is provided with holes for connection to the atmosphere, so as to act as a water seal valve which is adapted to ensure downstream constancy of the degree of vacuum, and is connected to a vacuum generator by means of a tube 6 made of elastic material.

The device 1 further comprises a blood collection chamber 7, which is delimited by side walls 7a and 7b, by a front wall, which is omitted in the drawing, by a rear wall, and finally by a bottom 7c.

The collection chamber 7 is divided into three sub-chambers by partitions 7d and 7e and has, proximate to the bottom, a cock 7f, which gives access to the tube 2 for connection to the bag 3, and a filter 7g, which receives the blood that arrives from the patient drainage system by means of a tube 8, which is made of elastic material.

The water seal is interposed between the two described chambers and comprises two ducts 9 and 10 which are connected at the lower end and in which water is provided in a known manner up to a certain level, by means of a hole 9a of the duct 9 which is open onto the portion of space delimited by a bottom 11.

The duct 9 is delimited at the front by composite wall 9b, 9c, 9d, 9e, 9f, by the composite rear wall, generally designated by the reference numeral 9g, and by the side walls 5b and 12, and is connected, at the upper end, to the suction control chamber 5 by means of the labyrinth 5d, which allows air to pass without hindrance and prevents as much as possible the transfer of water as might be caused by accidental tipping.

The duct 10, which is delimited at the rear by a composite wall generally designated by the reference numeral 10a and is laterally delimited by the walls 12 and 7a, is delimited at the front by a composite wall 10b, 10c, 10d, 10e, 10f; in particular, the region 10f is open at the portion from which the ribs such as 10g extend; the ribs, together with the wall 10h that is visible in FIG. 1, delimit passages which open onto the duct 10 and onto the blood collection chamber 7, connecting them.

One of the important characteristics of the invention consists of the presence of the membrane 13, which is kept rested against the wall region 10f and more precisely against teeth 10i that protrude from it, by a secondary frame 13a.

The membrane 13, which is thus interposed at the inlet of the above-described passages for connection between the duct 10 of the water seal and the blood collection chamber 7, is made of a material which is hydrophobic, so as to prevent the bidirectional passage of liquids, and sterilizes the air that passes through it.

According to a different embodiment, in the region for the connection of the duct 10 to the chamber 7 there are mechanical means, such as a labyrinth or an expansion chamber, which are adapted to prevent the passage of liquids, and a membrane which sterilizes the air that passes through it.

The duct 10 includes the maximum negative pressure valve, which comprises a slider formed by a ball 14, which when inactive rests against the wall portion 10c.

When the water tends to rise in the duct 10, drawn by an excess of negative pressure in the chamber 7, the ball is drawn upward up to the vicinity of a seat 15, which is larger than the ball, and is blocked in a suitable position by the presence of an abutment 16 against which it collides; this produces a resistance to the flow of water which contains within physiological values the maximum negative pressure in the chamber 7.

The description of the water seal is completed by noting the presence, at the top of the duct 9, of a positive pressure valve 17, which is adapted to vent air, and, at the top of the duct 10, of a tube 18 which is connected to the atmosphere and is provided by means of a tube made of elastic material.

The reference numeral 19 further designates a screw provided with an actuation knob which is adapted to move into contact with the tube 6, so as to provide a partial reduction of the passage area, with consequent coarse adjustment of the suction conditions.

Figure 2:
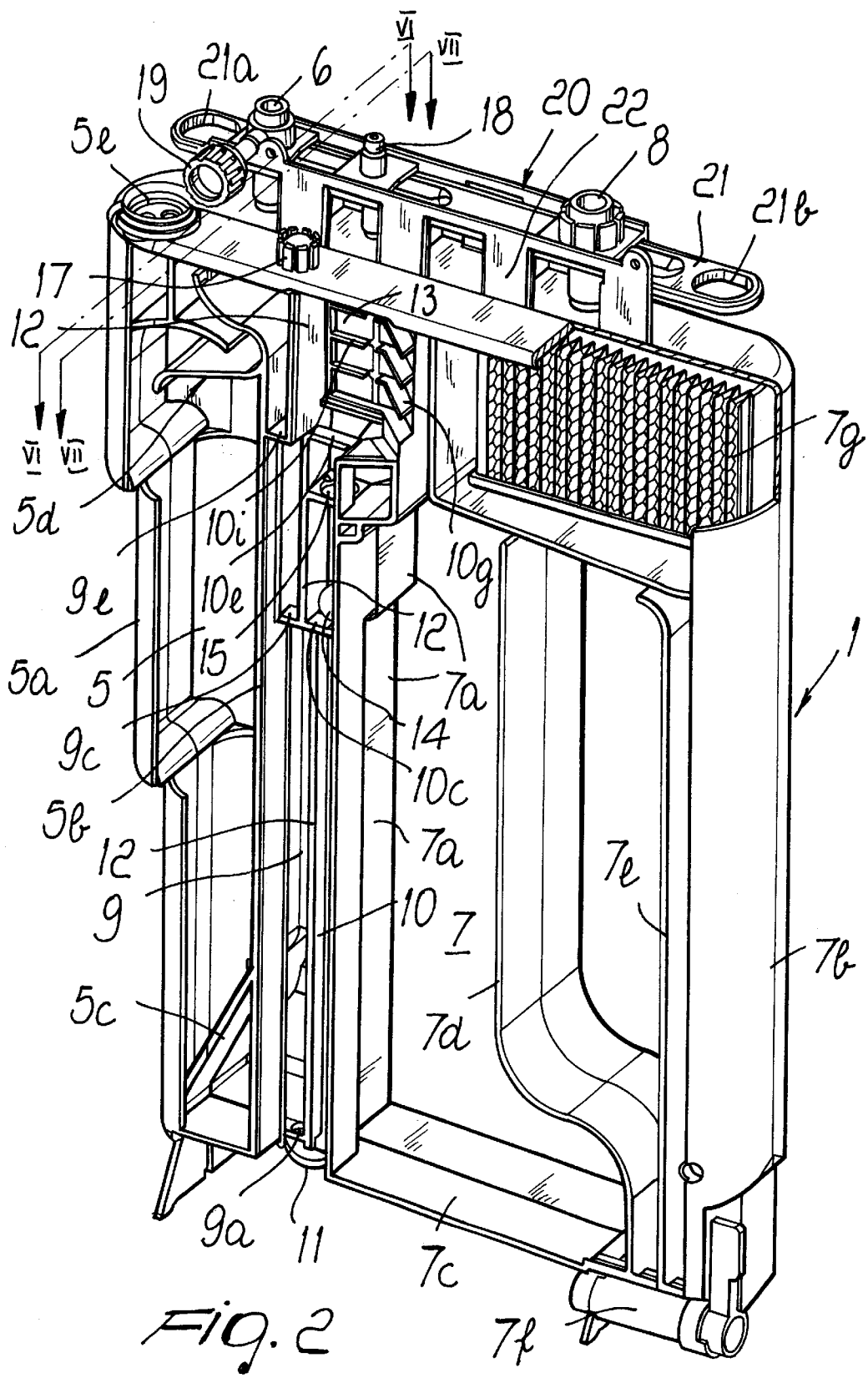
FIG. 2 is a cutout perspective view of the device according to the invention.
Figure 3:
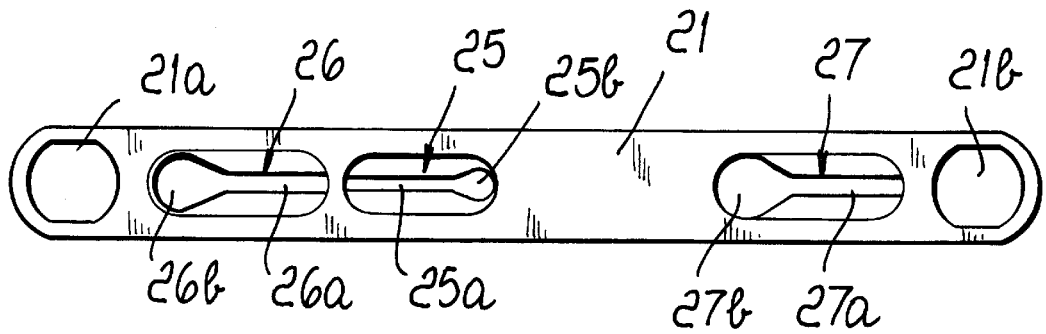
FIG. 3 is a front view of a detail of the device.
Figure 4:
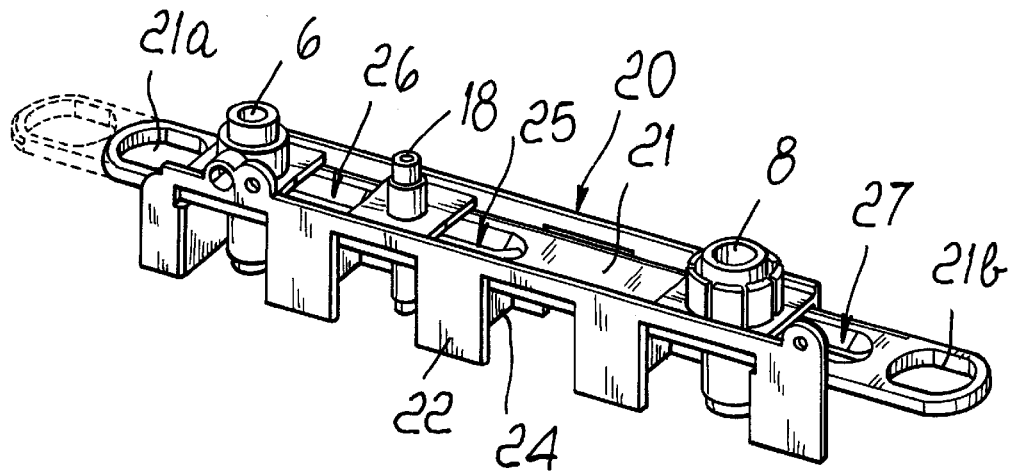
FIGS. 4 and 5 are perspective views of a detail of the device in two different steps of operation.
Figure 5:
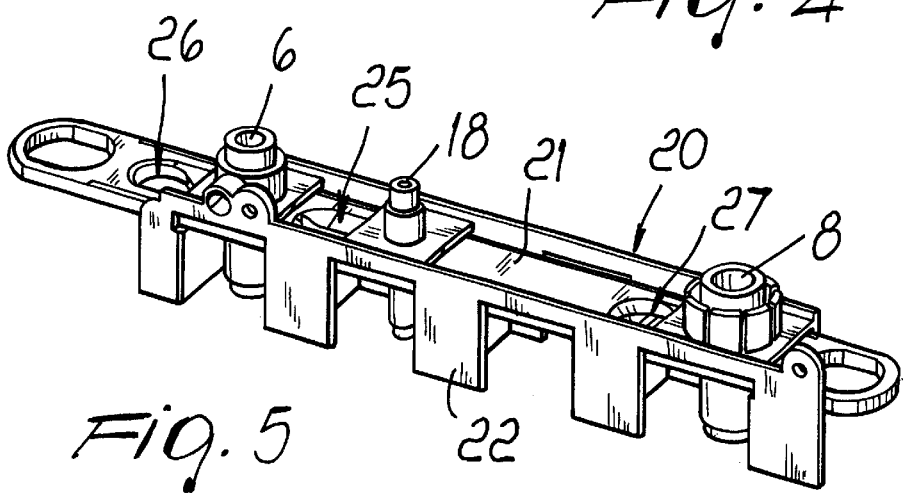
Figure 6:
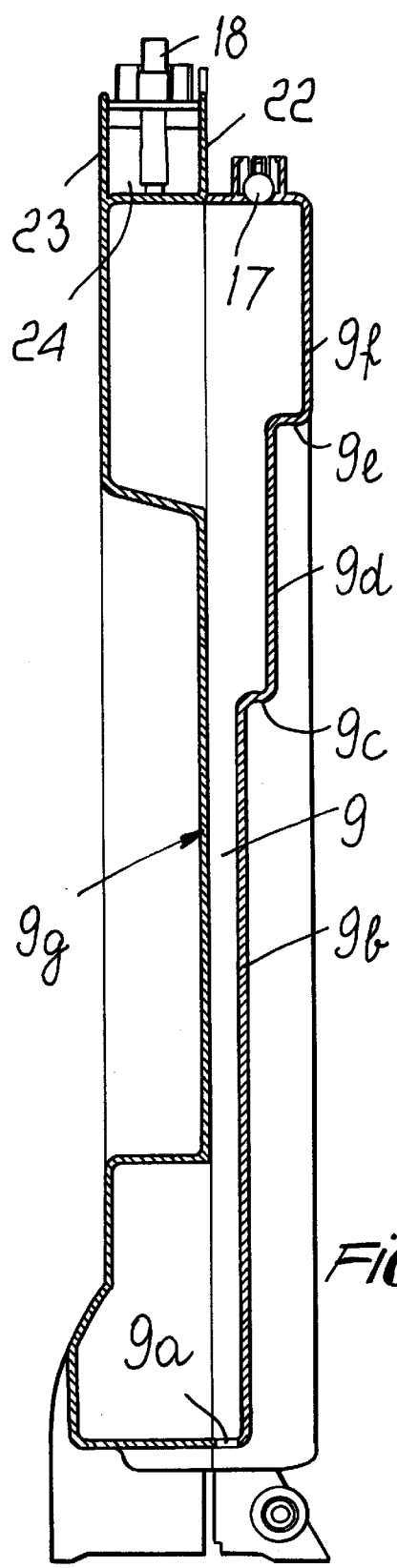
FIGS. 6 and 7 are sectional views, taken respectively along the planes VI—VI and VII—VII of FIG. 2.
Figure 7:
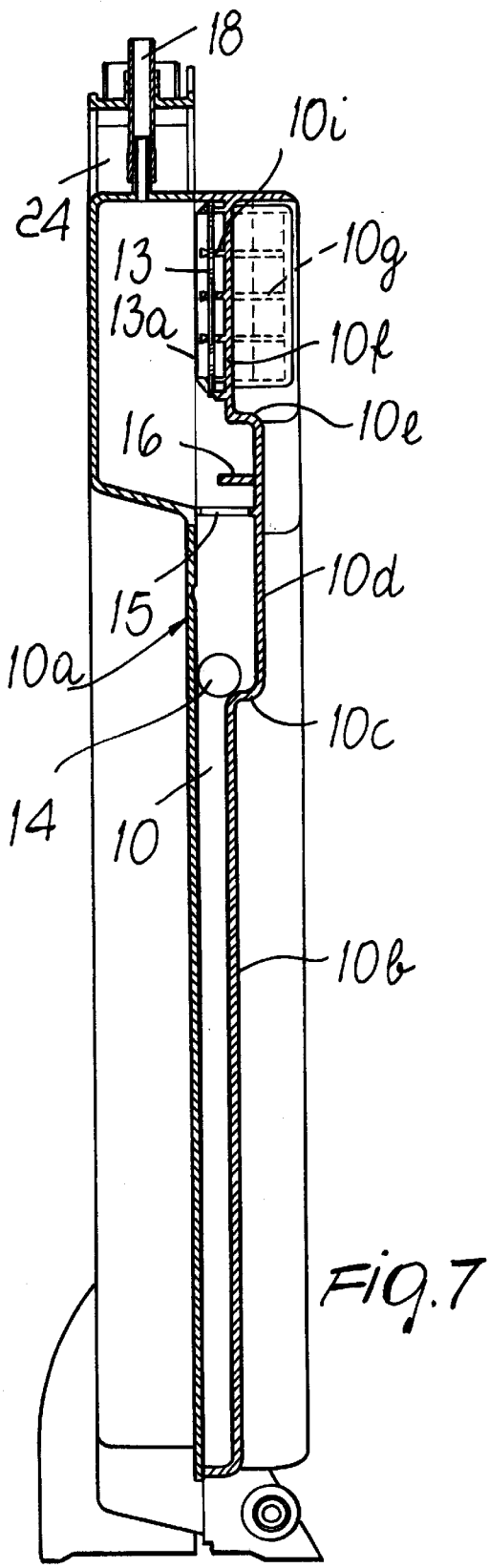

The described invention is provided with means, generally designated by the reference numeral 20, which are adapted to act simultaneously on the tubes made of elastic material 6, 18 and 8 so as to selectively provide a condition in which the tube 18 for connection to the atmosphere is closed and the tubes 6 and 8, respectively connected to a vacuum generator and to the patient drainage system, are open, as shown in FIGS. 1, 2 and 4 and to be used in an operating step during which the chamber 7 is filled with blood from the patient, and a condition in which the tube 18 is open and the tubes 6 and 8 are closed, as shown in FIG. 5, to be adopted in the operating step in which the blood is transferred by gravity from the chamber 7 to the bag 3, and also in another step described hereafter.

Means 20 comprise a plate 21, which can slide between two extreme positions: the first extreme position is shown in FIGS. 1, 2 and 4, and the latter figure, which shows separately and in enlarged scale the detail shown in FIG. 2, illustrates with a dashed line the second extreme position shown in FIG. 5.

The plate 21 is supported by a bridge formed by walls 22 and 23, which protrude from the cover of the device and are connected by transverse elements, such as 24, and is provided not only with end handles 21a, 21b but also with openings, each of which allows the passage of one tube: an opening 25 for the tube 18, an opening 26 for the tube 6, an opening 27 for the tube 8.

The openings are longitudinally elongated, so that each tube is at one end of the corresponding opening when the plate 21 is at one end of its stroke, and are shaped so as to form different portions.

The opening 25 has a portion 25a, which produces a constriction of the tube 18, with consequent closure thereof, and a wider portion 25b, which allows the free passage of the tube and which is present at the end that is directed toward the handle 21b.

The openings 26 and 27 have portions 26a, 27a, which determine a constriction of the tubes 6 and 8, respectively, with consequent closure thereof, and wider portions 26b and 27b, which allow the free passage of the tubes, provided at the end that is directed toward the handle 21a.

When the plate 21 is in the position shown in FIGS. 1, 2 and 4, the tubes 6 and 8 are inserted in the wider portions 26b, 27b and are thus open, while the tube 18 is inserted in the portion 25a and is therefore closed.

Clearly, by pulling the plate 21 into the position of FIG. 5 the tubes 6 and 8 are closed, since they are placed at the portions 26a and 27a, while the tube 18 is opened, since it is placed at the wider portion 25b.

It is noted that this situation is determined not only in order to transfer blood from the chamber 7 to the bag 3 mentioned earlier but also in order to allow the venting of the high negative intrathoracic pressure of the patient without any risk of trapping air in the case of gravity drainage.

The described invention is susceptible of numerous modifications and variations, all of which are within the scope of the inventive concept; thus, for example, the tubes 6, 8 and 18 can be made of a material which is even plastically deformable.

The means adapted to act on said tubes may be provided in any manner, and indeed said means may be shaped so as to act simultaneously only on the tubes that are connected to the atmosphere and to the patient drainage system.

The disclosures in Italian Patent Application No. MN99A000050 from which this application claims priority are incorporated herein by reference.

What is claimed is:

1. A device for postoperative autotransfusion particularly in heart surgery, comprising, functionally connected in a monolithic unit: a suction control chamber, which is adapted to be connected to a vacuum generator by means of a tube; a blood collection chamber, which is provided at a bottom thereof with a cock adapted to be connected to a bag and adapted to be connected by means of at least one tube to a drainage system of a patient; and a water seal, which is interposed between said control chamber and said collection chamber and comprises two ducts which are interconnected at a lower end and are connected, at an upper end, respectively to the suction control chamber and to the blood collection chamber, a union being provided proximate to an end that is connected to said blood collection chamber, said union being connected to the atmosphere by means of a tube, the device further comprising means which are adapted to act simultaneously at least on said tubes respectively connected to the atmosphere and to the drainage system of the patient, so as to selectively provide a condition in which the tube connected to the atmosphere is closed and the tube connected to the patient drainage system is open, and a condition in which said tube connected to the atmosphere is open and said tube connected to the patient drainage system is closed.

2. The device according to claim 1, comprising a tube connected to a vacuum generator and wherein said means are adapted to act simultaneously on the tubes connected respectively to the atmosphere, to the vacuum generator, and to the patient drainage system, so as to selectively provide a condition in which the tube connected to the atmosphere is closed and the tubes connected respectively to the vacuum generator and to the patient drainage system are open, and a condition in which said tube connected to the atmosphere is open and said tubes connected respectively to a vacuum generator and to the patient drainage system are closed.

3. The device according to claim 2, wherein the means adapted to act simultaneously on the tubes connected respectively to the atmosphere, to the vacuum generator and to the patient drainage system comprise a plate which can slide between two extreme positions and is provided with openings, each of said openings being adapted to allow the passage of one of said tubes, said openings being longitudinally elongated, so that each tube lies at one end of a respective opening when said plate is at one end of its stroke, said openings being shaped so as to determine a constriction of the corresponding tube, with consequent closure thereof, the opening that allows the passage of the tube that is connected to the atmosphere having a wider portion so as to determine the free passage of the tube at the end that is directed toward one of the ends of the sliding plate, while the openings that allow the passage of the tubes that are connected respectively to a vacuum generator and to the patient drainage system have a similar wider portion at the end that is directed toward the other end of said sliding plate.

4. A device for postoperative autotransfusion particularly in heart surgery, comprising, functionally connected in a monolithic unit: a suction control chamber, which is adapted to be connected to a vacuum generator by means of a tube; a blood collection chamber, which is provided at a bottom thereof with a cock adapted to be connected to a bag and adapted to be connected by means of at least one tube to a drainage system of a patient; and a water seal, which is interposed between said control and collection chambers and comprises two ducts which are interconnected at a lower end and are connected, at an upper end, respectively to the suction control chamber and to the blood collection chamber, a union being provided proximate to an end that is connected to said blood collection chamber, said union being connected to the atmosphere by means of a tube, wherein means adapted to prevent the passage of liquids and allow the passage of air and sterilize said air are interposed between the water seal and the blood collection chamber.

5. The device according to claim 4, wherein the means interposed between the water seal and the blood collection chamber comprise a membrane which is hydrophobic and sterilizes the air that passes through it.

6. The device according to claim 4, wherein the means interposed between the water seal and the blood collection chamber comprise mechanical means adapted to prevent the passage of liquids and a membrane which sterilizes the air that passes through it.

7. A device for postoperative autotransfusion particularly in heart surgery, comprising, functionally connected in a monolithic unit: a suction control chamber, which is adapted to be connected to a vacuum generator by means of a tube; a blood collection chamber, which is provided at a bottom thereof with a cock adapted to be connected to a bag and adapted to be connected by means of at least one tube to a drainage system of a patient; and a water seal, which is interposed between said control and collection chambers and comprises two ducts which are interconnected at a lower end and are connected, at an upper end, respectively to the suction control chamber and to the blood collection chamber, the duct connected to the blood collection chamber being provided with a maximum negative pressure valve which comprises a slider which can move by hydrodynamic entrainment effect in contrast with the force of gravity from a lower position on a supporting platform, wherein an abutment is provided which is adapted to delimit, in an upward region, a stroke of a movable slider proximate to a passage opening which is larger than the slider, up to an adapted position with respect to said passage opening.

8. The device according to claim 2, comprising a screw which is provided with an actuation knob at one end and is adapted to move, at an other end, into contact with the tube which is connected to the vacuum generator, so as to provide a partial reduction of the passage area of said tube with consequent coarse adjustment of the suction conditions.

* * * * *